United States Patent
Siddall et al.

(10) Patent No.: US 9,216,958 B2
(45) Date of Patent: Dec. 22, 2015

(54) 2,6-DIHALO-5-ALKOXY-4-SUBSTITUTED-PYRIMIDINES, PYRIMIDINE-CARBALDEHYDES, AND METHODS OF FORMATION AND USE

(71) Applicant: DOW AGROSCIENCES LLC, Indianapolis, IN (US)

(72) Inventors: Thomas Lyman Siddall, Zionsville, IN (US); Joshua John Roth, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/505,380

(22) Filed: Oct. 2, 2014

(65) Prior Publication Data

US 2015/0031883 A1  Jan. 29, 2015

Related U.S. Application Data

(62) Division of application No. 13/730,406, filed on Dec. 28, 2012, now Pat. No. 8,877,925.

(60) Provisional application No. 61/582,156, filed on Dec. 30, 2011.

(51) Int. Cl.
| | | |
|---|---|---|
| C07D 239/34 | (2006.01) | |
| C07D 405/04 | (2006.01) | |
| C07D 239/47 | (2006.01) | |
| A01N 43/54 | (2006.01) | |

(52) U.S. Cl.
CPC .............. *C07D 239/34* (2013.01); *A01N 43/54* (2013.01); *C07D 239/47* (2013.01); *C07D 405/04* (2013.01)

(58) Field of Classification Search
CPC .................................................. C07D 239/34
See application file for complete search history.

(56) References Cited

U.S. PATENT DOCUMENTS

| | | |
|---|---|---|
| 7,642,220 B2 | 1/2010 | Epp et al. |
| 2007/0179059 A1 | 8/2007 | Epp et al. |
| 2009/0062125 A1 | 3/2009 | Epp et al. |
| 2009/0264293 A1 | 10/2009 | Siddall et al. |
| 2010/0041556 A1 | 2/2010 | Epp et al. |
| 2010/0121058 A1 | 5/2010 | Guenthenspberger et al. |
| 2013/0172557 A1 | 7/2013 | Siddall et al. |

FOREIGN PATENT DOCUMENTS

| | | |
|---|---|---|
| WO | 2005063721 | 7/2005 |
| WO | 2007082076 | 7/2007 |
| WO | 2009029735 | 3/2009 |
| WO | 2011080568 | 7/2011 |
| WO | 2011141848 | 11/2011 |

OTHER PUBLICATIONS

American Chemical Society (ACS) STN Chemical Abstract Service (CAS) Registry Database. Updated (c) 2013.
Epifani, E., et al., "Regioselective allylation and propargylation of pyrimidines," Tetrahedron 1989, pp. 2075-2082, vol. 45, No. 2.
Ivin, B.A., et al.., "Unsaturated hydantoin derivatives Synthesis and rearrangement of some ethyl esters of α-substituted hydantoin-Δ5,α-acetic acids," 1976, ages 1342-1349.
Koch, Uwe, et al., "2-(2-thienyl)-5,6-dihydroxy-4-carboxypyrimidines as inhibitors of the hepatitis C virus NS5B polymerase: discovery, SAR, modeling, and mutagenesis," J. Med Chem, 2006, pp. 1693-1705, vol. 49.
Strekowski, Lucjan, et al., "Synthesis of 2-chloro-4-6-di(heteroaryl)pyrimidines," J. Heterocyclic Chem, 1990, pp. 1393-1400 , vol. 27.
International Search Report and Written Opinion for PCT Application No. PCT/US2012/072121, mailed Apr. 29, 2013.

*Primary Examiner* — Noble Jarrell
*Assistant Examiner* — John S Kenyon
(74) *Attorney, Agent, or Firm* — Michael J. Terapane; Traskbritt, P.C.

(57) ABSTRACT

2,6-Dihalo-5-alkoxy-4-substituted-pyrimidines, 2,6-dihalo-5-alkoxy-4-pyrimdine carbaldehydes, and derivatives of each are useful intermediates in forming potent herbicides that demonstrate a broad spectrum of weed control. These compounds are disclosed, as are methods of forming and using these compounds.

16 Claims, No Drawings

2,6-DIHALO-5-ALKOXY-4-SUBSTITUTED-PYRIMIDINES, PYRIMIDINE-CARBALDEHYDES, AND METHODS OF FORMATION AND USE

CROSS-REFERENCE TO RELATED APPLICATION

This application is a divisional of U.S. patent application Ser. No. 13/730,406, filed Dec. 28, 2012, pending, which application claims the benefit of U.S. Provisional Patent Application Ser. No. 61/582,156, filed Dec. 30, 2011, the disclosure of each of which is hereby incorporated herein in its entirety by this reference.

TECHNICAL FIELD

Embodiments of the present disclosure relate to 2,6-dihalo-5-alkoxy-4-substituted pyrimidines. Embodiments of the present disclosure also related to 2,6-dihalo-5-alkoxy-4-pyrimidine carbaldehydes. Embodiments of the present disclosure further relate to methods of forming 2,6-dihalo-5-alkoxy-4-substituted-pyrimidines and 2,6-dihalo-5-alkoxy-4-pyrimidine carbaldehydes and methods of using the same.

BACKGROUND 2,6-dihalo-5-alkoxy-pyrimidine-4-carboxylic acids and esters are useful intermediates for the preparation of pharmaceutical and agricultural chemicals, such as herbicides. Conventional methods to form these compounds may be laborious, low yielding, and not easily scalable.

BRIEF SUMMARY

An embodiment of the present disclosure includes compounds of Formula I:

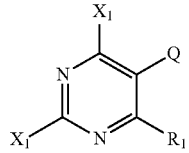

wherein
$X_1$ represents a halogen;
$R_1$ represents a hydrocarbon chain; and
Q represents a $C_1$-$C_2$ alkoxy.

In particular embodiments, compounds of Formula I independently include those in which $X_1$ represents chlorine, wherein Q represents methoxy, and wherein $R_1$ represents a hydrocarbon chain oxidizable to an acid, for example, without limitation, an alkyl, vinylic, aryl, alkenyl, or furanyl, with $R_1$ representing vinylic being most preferred.

Another embodiment of the present disclosure includes compounds of Formula II:

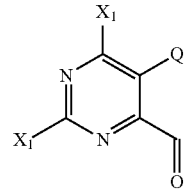

wherein
$X_1$ represents a halogen; and
Q represents a $C_1$-$C_2$ alkoxy.

Representative compounds of Formula II independently include those in which $X_1$ represents chlorine and wherein Q represents methoxy.

Another embodiment of the present disclosure includes a method of forming a compound of Formula II, i.e., a 2,6-dihalo-5-alkoxy-pyrimidine-4-carbaldehyde, by reacting a compound of Formula I, i.e., a 2,6-dihalo-5-alkoxy-4-substituted pyrimidine with an oxidant.

Yet another embodiment of the present disclosure includes a method of forming a compound of Formula I, i.e., a 2,6-dihalo-5-alkoxy-4-substituted pyrimidine, comprising reacting a 2,6-dihalo-5-alkoxy pyrimidine with an organometallic reagent to form a 2,6-dihalo-5-alkoxy-4-substituted-3-(metal-halo or metal) pyrimidine and oxidizing the 2,6-dihalo-5-alkoxy-4-substituted-3-(metal-halo or metal) pyrimidine to form the 2,6-dihalo-5-alkoxy-4-substituted pyrimidine.

Another particular embodiment of the present disclosure includes a method of using a 2,6-dihalo-5-alkoxy-4-substituted pyrimidine to form an alkyl 6-amino-2-halo-5-alkoxy-pyrimidine-4-carboxylate. The 2,6-dihalo-5-alkoxy-4-substituted pyrimidine comprises a pyrimidine ring comprising a 4 position and a 6 position. The pyrimidine ring comprises a hydrocarbon chain at the 4 position. The pyrimidine ring comprises a halogen at the 6 position. The method of using the 2,6-dihalo-5-alkoxy-4-substituted pyrimidine comprises contacting the hydrocarbon chain at the 4 position with an oxidant to form a carbonyl group at the 4 position. The carbonyl group is contacted at the 4 position with bromine in an alcohol to form a carboalkoxy group at the 4 position. The halogen is contacted at the 6 position with an amine to form an amino group at the 6 position.

DETAILED DESCRIPTION

As used herein, the term "alkyl" refers to an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

As used herein, the term "alkoxy" refers to an alkyl group bonded to an oxygen, for example, methoxy and ethoxy.

As used herein, the term "halo" refers to fluoro, chloro, bromo, and iodo.

As used herein, the term "halogen" refers to fluorine, chlorine, bromine, and iodine.

As used herein, the term Grignard reagent refers to an organomagnesium halide.

Compounds of Formula I, as follows, are useful intermediates in forming compounds used in preparing pharmaceutical and agricultural chemicals, such as herbicides:

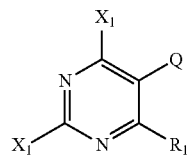

wherein
$X_1$ represents a halogen;
$R_1$ represents a hydrocarbon chain; and
Q represents a $C_1$-$C_2$ alkoxy.

Such 2,6-dihalo-5-alkoxy-4-substituted pyrimidines may include a pyrimidine ring having halogens at the 2 and 6 positions, a $C_1$-$C_2$ alkoxy group at the 5 position, and a hydrocarbon chain at the 4 position. The halogens at the 2 and 6 positions may be chlorine, such that the compound may be a 2,6-dichloro-5-alkoxy-4-substituted pyrimidine. The alkoxy group at the 5 position may be methoxy, such that the compound may be a 2,6-dihalo-5-methoxy-4-substituted pyrimidine. The hydrocarbon chain at the 4 position is a hydrocarbon group oxidizable to an acid. The chain may include, for example and without limitation, an alkyl, vinylic, aryl, alkenyl, or furanyl group. In some embodiments, the hydrocarbon chain at the 4 position may be a vinylic group, such that the compound is a 2,6-dihalo-5-alkoxy-4-vinylic pyrimidine. The compound of Formula I may be 2,6-dichloro-5-methoxy-4-vinylic pyrimidine.

Compounds of Formula II, as follows, are also useful intermediates in forming compounds used in preparing pharmaceutical and agricultural chemicals, such as herbicides:

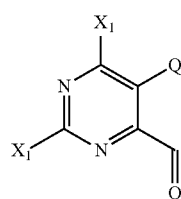

wherein
  $X_1$ represents a halogen; and
  Q represents a $C_1$-$C_2$ alkoxy.

Such 2,6-dihalo-5-alkoxy-pyrimidine-4-carbaldehydes can include a pyrimidine ring having halogens at the 2 and 6 positions, a $C_1$-$C_2$ alkoxy group at the 5 position, and a carbonyl group at the 4 position. The halogens at the 2 and 6 positions may be chlorine, such that the compound may be a 2,6-dichloro-5-alkoxy-pyrimdine-4-carbaldehyde. The alkoxy group at the 5 position may be methoxy, such that the compound may be a 2,6-dihalo-5-methoxy-pyrimidine-4-carbaldehyde. The compound of Formula II may be 2,6-dichloro-5-methoxy-pyrimidine-4-carbaldehyde.

One embodiment of forming a compound of Formula II using a compound of Formula I is shown in Scheme 1, as follows:

Scheme 1

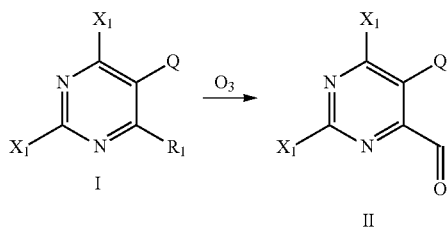

As shown in Scheme 1, a compound of Formula II, i.e., a 2,6-dihalo-5-alkoxy-pyrimidine-4-carbaldehyde, can be prepared by oxidizing a compound of Formula I, i.e., a 2,6-dihalo-5-alkoxy-4-substituted pyrimidine. The method of Scheme 1 includes reacting a compound of Formula I with an oxidant to form a compound of Formula II.

In this case, $X_1$ represents a halogen; Q represents a $C_1$-$C_2$ alkoxy; and $R_1$ represents a hydrocarbon chain. The oxidant may be ozone ($O_3$).

The method of Scheme 1 includes contacting the hydrocarbon chain at the 4 position of the pyrimidine ring of the compound of Formula I with an oxidant to form a carbonyl group at the 4 position of the pyrimidine ring in the resulting compound of Formula II. Thus, the compound of Formula II may be the carbaldehyde derivative of the compound of Formula I.

The method of Scheme 1 may include introducing the oxidant with a solvent. The solvent may be a halogenated solvent, e.g., dichloromethane (DCM). The solvent may be methanol.

The method of Scheme 1 is illustrated in each of Examples 6 and 7.

One embodiment of forming a compound of Formula I is shown in Scheme 2, as follows:

Scheme 2

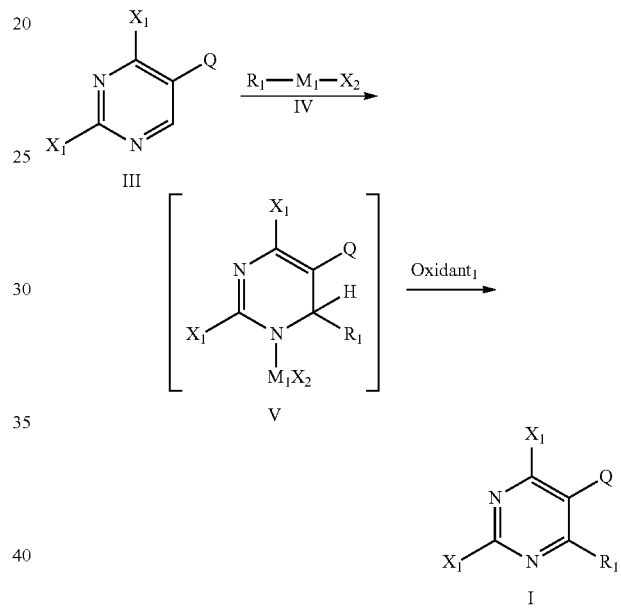

As shown in Scheme 2, a compound of Formula I, i.e., a 2,6-dihalo-5-alkoxy-4-substituted pyrimidine, can be prepared using a compound of Formula III, i.e., a 2,6-dihalo-5-alkoxy pyrimidine. The method of Scheme 2 includes reacting a compound of Formula III with an organometallic reagent of Formula IV to form an intermediate of Formula V and reacting the intermediate of Formula V with an oxidant to form a compound of Formula I.

In this case, $X_1$ represents a halogen; Q represents a $C_1$-$C_2$ alkoxy; $R_1$ represents a hydrocarbon chain that is oxidizable to an acid, e.g., an alkyl, vinylic, or aryl. $M_1$ represents magnesium; and $X_2$ represents bromine, iodine, or chlorine; or $M_1$-$X_2$ and $M_1X_2$ represent, together, lithium. "Oxidant$_1$" may be an appropriate oxidant, e.g., an organic oxidant such as 2,3-dichloro-5,6-dicyano-p-benzoquinone (DDQ); an inorganic oxidant such as manganese dioxide ($MnO_2$); a halogen-based oxidant; or atmospheric oxygen in a metal-catalyzed oxidation reaction.

The organometallic reagent of Formula IV may be a Grignard reagent, such that $M_1$ represents magnesium and $X_1$ represents a halogen. The Grignard reagent may be a magnesium bromide reagent. For example, without limitation, the Grignard reagent may be vinyl magnesium bromide. Use of an organo-magnesium bromide Grignard reagent may be conducive for carrying out the method of Scheme 2 at temperatures near room temperature or, alternatively, at temperatures near or greater than 0° C. The organometallic reagent of Formula IV may alternatively be an organolithium reagent such that $M_1$ represents lithium. Use of an organolithium reagent may further include carrying out Scheme 2 at temperatures at or below −40° C.

Reacting a compound of Formula III with the organometallic reagent of Formula IV may form an intermediate compound of Formula V, i.e., an anionic 2,6-dihalo-5-alkoxy-4-substituted-3-(metal-halo or metal) pyrimidine. In embodiments in which the organometallic reagent of Formula IV is a Grignard reagent, the resulting intermediate compound of Formula V is an anionic 2,6-dihalo-5-alkoxy-4-substituted-3-metal-halo pyrimidine. In embodiments in which the organometallic reagent of Formula IV is an organolithium reagent, the resulting intermediate compound of Formula V is an anionic 2,6-dihalo-5-alkoxy-4-substituted-3-metal pyrimidine.

The organometallic reagent of Formula IV may be provided with a solvent appropriate for an organometallic reagent reaction, such as tetrahydrofuran (THF); 1,4-dioxane; diethyl ether; dimethyl oxide; or dimethoxyethane.

Reacting the compound of Formula III with the organometallic halide reagent of Formula IV may form a hydrocarbon chain at the 4 position of the pyrimidine ring and may form a metal halide or metal group, i.e., a metal (halide) group, at the 3 position of the pyrimidine ring. Reacting the intermediate compound of Formula V with an appropriate oxidant may form a compound of Formula I, with the hydrocarbon chain at the 4 position of the pyrimidine ring.

The method of Scheme 2 may further include introducing a proton source to the reaction. The proton source may be wet acetone, acetic acid, or a similarly-functioning compound.

The method of Scheme 2 may be accomplished without isolation of the intermediate compound of Formula V. Therefore, the oxidation to form a compound of Formula I may be accomplished in situ. The prepared compound of Formula I may or may not be isolated before use thereof.

The method of Scheme 2 is illustrated in each of Examples 1 through 5.

One embodiment of using a compound of Formula II to form a compound of Formula VII is shown in Scheme 3, as follows:

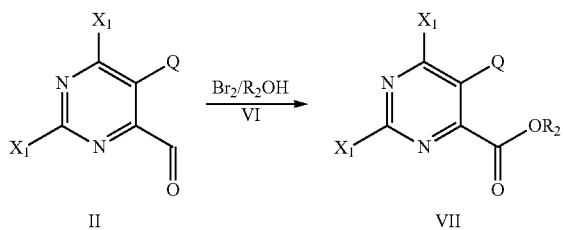

As shown in Scheme 3, a compound of Formula VII, i.e., an alkyl 2,6-dihalo-5-alkoxy-pyrimidine-4-carboxylate, can be prepared using a compound of Formula II, i.e., a 2,6-dihalo-5-alkoxy-pyrimidine-4-carbaldehyde.

In this case, $X_1$ represents a halogen; Q represents a $C_1$-$C_2$ alkoxy; and $R_2$ represents an alkyl. $R_2$ may represent methyl.

The method of Scheme 3 includes contacting the carbonyl group at the 4 position of the pyrimidine ring of the compound of Formula II with bromine in an alcohol of Formula VI to form a carboalkoxy group at the 4 position of the pyrimidine ring in the resulting compound of Formula VII.

Accordingly, the method of Scheme 3 provides a method of using a compound of Formula II to prepare a compound of Formula VII. Also, the combined methods of Schemes 1 and 3 provide a method of using a compound of Formula I to prepare a compound of Formula VII. Also, the combined methods of Schemes 1, 2, and 3 provide a method of using a compound of Formula III to prepare a compound of Formula VII. Formed compounds may or may not be isolated between combined schemes.

The method of Scheme 3 is illustrated in each of Examples 8 and 9.

One embodiment of using a compound of Formula VII to form a compound of Formula IX is shown in Scheme 4, as follows:

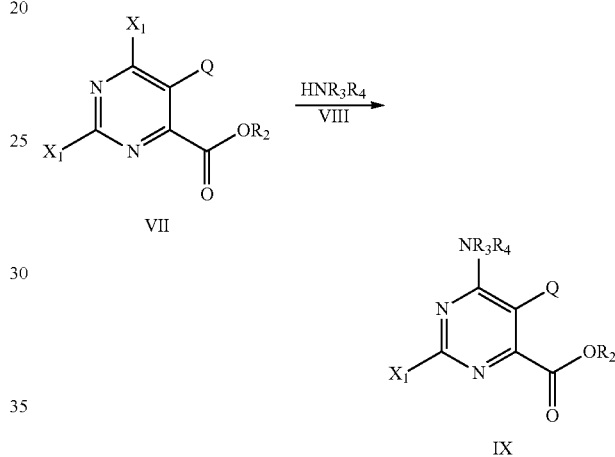

As shown in Scheme 4, a compound of Formula IX, i.e., an alkyl 6-amino-2-halo-5-alkoxy-pyrimidine-4-carboxylate, can be prepared using a compound of Formula VII, i.e., an alkyl 2,6-dihalo-5-alkoxy-pyrimidine-4-carboxylate. The method of Scheme 4 includes reacting the compound of Formula VII with an amine of Formula VIII (or salts thereof) to form the compound of Formula IX.

In this case, $X_1$ represents a halogen; Q represents a $C_1$-$C_2$ alkoxy; $R_2$ represents an alkyl; and $R_3$ and $R_4$ independently represent H, $C_1$-$C_6$ alkyl, $C_3$-$C_6$ alkenyl, $C_3$-$C_6$ alkynyl, hydroxyl, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, or $C_1$-$C_6$ dialkyl phosphonyl, or $R_3$ and $R_4$ taken together with N represent a 5- or 6-membered saturated ring.

The method of Scheme 4 may further include use of a solvent. For example, without limitation, a solvent used in the method may include dimethyl sulfoxide.

The method of Scheme 4 includes contacting the halogen at the 6 position of the pyrimidine ring of the compound of Formula VII with an amine of Formula VIII to form an amino group at the 6 position of the pyrimidine ring in the resulting compound of Formula IX.

Accordingly, the method of Scheme 4 provides a method of using a compound of Formula VII to prepare a compound of Formula IX. Also, the combined methods of Schemes 3 and 4 provide a method of using a compound of Formula II to prepare a compound of Formula IX. Also, the combined methods of Schemes 1, 3, and 4 provides a method of using a compound of Formula I to prepare a compound of Formula IX. Also, the combined methods of Schemes 1 through 4 provides a method of using a compound of Formula III to prepare a compound of Formula IX. Formed compounds may or may not be isolated between combined schemes.

The method of Scheme 4 is illustrated in each of Examples 10 and 11. Other embodiments and examples of this method are described in U.S. Pat. No. 7,642,220 to Epp et al. ("Scheme 2" therein), the disclosure of which is incorporated by reference herein.

One embodiment of using a compound of Formula IX to form a compound of Formula XI is shown in Scheme 5, as follows:

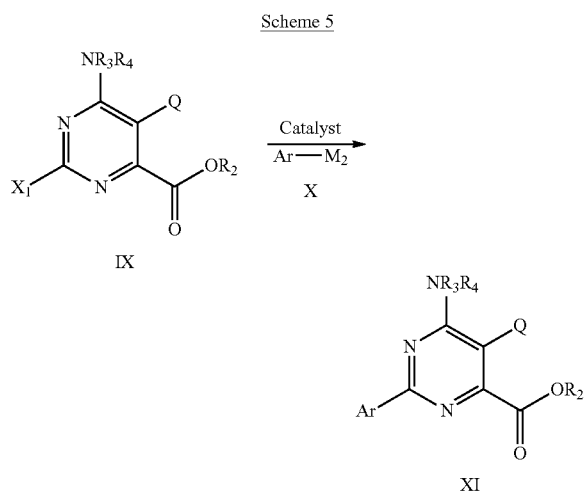

As shown in Scheme 5, a compound of Formula XI, i.e., an alkyl 2-(substituted phenyl)-6-amino-5-alkoxy-pyrimidine-4-carboxylate, can be prepared using a compound of Formula IX, i.e., an alkyl 6-amino-2-halo-5-alkoxy-pyrimidine-4-carboxylate. The method of Scheme 5 includes reacting the compound of Formula IX with an organometallic compound of Formula X to form the compound of Formula XI. The method may include an inert solvent.

In this case, $X_1$ represents a halogen; Q represents a $C_1$-$C_2$ alkoxy; $R_2$ represents an alkyl; and $R_3$ and $R_4$ independently represent H, $C_1$-$C_6$ alkyl, $C_3$-$C_6$ alkenyl, $C_3$-$C_6$ alkynyl, hydroxyl, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, or $C_1$-$C_6$ dialkyl phosphonyl, or $R_3$ and $R_4$ taken together with N represent a 5- or 6-membered saturated ring.

Ar represents a phenyl group substituted with one or more substitutents selected from halogen, nitro, cyano, formyl, $C_1$-$C_6$ alkyl, $C_2$-$C_6$ alkenyl, $C_2$-$C_6$ alkynyl, $C_1$-$C_6$ alkoxy, $C_2$-$C_4$ alkoxyalkyl, $C_2$-$C_6$ alkylcarbonyl, $C_1$-$C_6$ alkylhio, $C_1$-$C_6$ alkylsulfinyl, $C_1$-$C_6$ alkylsulfonyl, $C_2$-$C_4$ alkenyloxy, $C_2$-$C_4$ alkynloxy, $C_2$-$C_4$ alkenylthio, $C_2$-$C_4$ alkynylthio, $C_1$-$C_6$ haloalkyl, $C_2$-$C_6$ haloalkenyl, $C_2$-$C_6$ haloalkynyl, $C_1$-$C_6$ haloalkoxy, $C_2$-$C_4$ haloalkoxyalkyl, $C_2$-$C_6$ haloalkylcarbonyl, $C_1$-$C_6$ haloalkylthio, $C_1$-$C_6$ haloalkylsulfinyl, $C_1$-$C_6$ haloalkylsulfonyl, $C_3$-$C_6$ trialkylsilyl, $C_2$-$C_4$ haloalkenyloxy, $C_2$-$C_4$ haloalkynyloxy, $C_2$-$C_4$ haloalkenylthio, $C_2$-$C_4$ haloalkynylthio, —OCH$_2$CH$_2$—, —OCH$_2$CH$_2$CH$_2$—, —OCH$_2$O—, —OCH2CH2O—, C(O)OR$_6$, —C(O)NR$_5$R$_6$, —CR$_5$NOR$_6$, —NR$_5$R$_6$, —NR$_5$OR$_6$, —NR$_5$SO$_2$R$_6$, —NR$_5$C(O)R$_6$, —NR$_5$C(O)OR$_6$, —NR$_5$C(O)NR$_5$R$_6$ or —NCR$_5$NR$_5$R$_6$. $R_5$ represents H, $C_1$-$C_4$ alkyl or $C_1$-$C_4$ haloalkyl. $R_6$ represents $C_1$-$C_4$ alkyl or $C_1$-$C_4$ haloalkyl.

$M_2$ can be tri-($C_1$-$C_4$ alkyl)tin or B(OR$_7$)(OR$_8$) where $R_7$ and $R_8$ are, independently of one another, hydrogen, $C_1$-$C_6$ alkyl, or when taken together form an ethylene or propylene group. "Catalyst" can be a transition metal catalyst, in particular a palladium catalyst such as bis(triphenylphosphine)palladium(II) dichloride.

The method of Scheme 5 includes replacing the halogen at the 2 position of the pyrimidine ring of the compound of Formula IX with the substituted phenyl group at the 2 position of the pyrimidine ring in the resulting compound of Formula XI.

Accordingly, the method of Scheme 5 provides a method of using a compound of Formula IX to prepare a compound of Formula XI. Also, the combined methods of Schemes 4 and 5 provide a method of using a compound of Formula VII to prepare a compound of Formula XI. Also, the combined methods of Schemes 3, 4, and 5 provide a method of using a compound of Formula II to prepare a compound of Formula XI. Also, the combined methods of Schemes 1, 3, 4, and 5 provide a method of using a compound of Formula I to prepare a compound of Formula XI. Also, the combined methods of Schemes 1 through 5 provide a method of using a compound of Formula III to prepare a compound of Formula XI. Formed compounds may or may not be isolated between combined schemes.

The method of Scheme 5 is illustrated in examples described in U.S. Pat. No. 7,642,220 to Epp et al. ("Scheme 1" therein), the disclosure of which is herein incorporated by reference.

Compounds of Formula XI and their corresponding carboxylic acids and/or salts are known to be superior herbicides with a broad spectrum of weed control against broadleaf weeds as well as grass and sedge weeds and with excellent crop selectivity at low use rates. These compounds further possess excellent toxicological or environmental profiles. The carboxylic acids of Formula XI are believed to be the compounds that actually kill or control undesirable vegetation. Analogs of these compounds in which the acid group or the carboalkoxy group of the pyrimidine carboxylic acid or ester is derivatized to form a related substituent that can be transformed within plants or the environment to an acid group or ester possess essentially the same herbicidal effect. Therefore, utilizing methods of Schemes 1 through 5, individually or in combination, one may use pyrimidine compounds of Formulas I, II, III, V, VII, and/or IX to prepare an herbicidal compound with Formula XI and/or agriculturally acceptable derivatives thereof. An "agriculturally acceptable derivative," when used to describe the carboxylate or carboxylic acid functionality at the 4 position, is defined as any salt, ester, carboxylic acid, acylhydrazide, imidate, thioimidate, amidine, amide, orthoester, acylcyanide, acyl halide, thioester, thionoester, dithiolester, nitrile or any other ester or acid derivative well known in the art that (a) does not substantially affect the herbicidal activity of the active ingredient, i.e., the 2-(substituted phenyl)-6-amino-5-alkoxy-4-pyrimidine-carboxylic acid, and (b) is or can be hydrolyzed, oxidized, or metabolized in plants or soil to the 2-(substituted phenyl)-6-amino-5-alkoxy-4-pyrimidine carboxylic acid or ester that, depending upon the pH, is in the dissociated or the undissociated form. The preferred agriculturally acceptable derivatives of the carboxylic acid are agriculturally acceptable salts, acids, esters and amides.

Another embodiment of using a compound of Formula I is shown in Scheme 6, as follows:

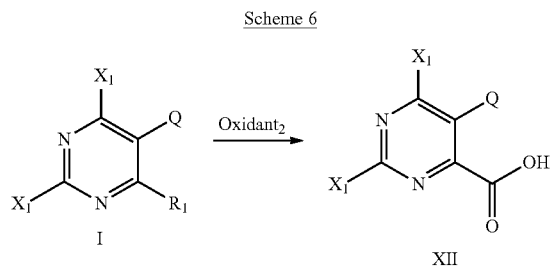

Scheme 6

As shown in Scheme 6, a compound of Formula XII, i.e., a 2,6-dihalo-5-alkoxy-pyrimidine-4-carboxylic acid, can be prepared using a compound of Formula I, i.e., a 2,6-dihalo-5-alkoxy-4-substituted pyrimidine.

In this case $X_1$ represents a halogen; Q represents a $C_1$-$C_2$ alkoxy; and $R_1$ represents a hydrocarbon chain. The hydrocarbon chain is oxidizable to an acid. For example, without limitation, the hydrocarbon chain may be an alkyl, vinylic, aryl, alkenyl, or furanyl. "Oxidant$_2$" represents an appropriate oxidant, e.g., potassium permanganate or oxygen in a catalyzed oxidation.

The method of Scheme 6 includes contacting the hydrocarbon chain at the 4 position of the pyrimidine ring of the compound of Formula I with an oxidant to form a carboxyl group at the 4 position of the pyrimidine ring of the resulting compound of Formula XII.

Accordingly, the method of Scheme 6 provides a method of using a compound of Formula I to prepare a compound of Formula XII. Also, the combined methods of Schemes 2 and 6 provide a method of using a compound of Formula III to prepare a compound of Formula XII. Formed compounds may or may not be isolated between combined schemes.

Still another embodiment of using a compound of Formula I is shown in Scheme 7, as follows:

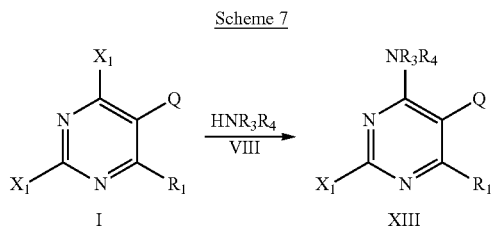

Scheme 7

As shown in Scheme 7, a compound of Formula XIII, i.e., a 6-amino-2-halo-5-alkoxy-4-substituted pyrimidine, can be prepared using a compound of Formula I, i.e., a 2,6-dihalo-5-alkoxy-4-substituted pyrimidine. The method of Scheme 7 includes reacting the compound of Formula I with an amine of Formula VIII to form the compound of Formula XIII.

In this case, $X_1$ represents a halogen; Q represents a $C_1$-$C_2$ alkoxy; $R_1$ represents a hydrocarbon chain; and $R_3$ and $R_4$ independently represent H, $C_1$-$C_6$ alkyl, $C_3$-$C_6$ alkenyl, $C_3$-$C_6$ alkynyl, hydroxyl, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, or $C_1$-$C_6$ dialkyl phosphonyl, or $R_3$ and $R_4$ taken together with N represent a 5- or 6-membered saturated ring.

The method of Scheme 7 may further include use of a solvent. For example, without limitation, a solvent used in the method may include dimethyl sulfoxide.

The method of Scheme 7 includes contacting the halogen at the 6 position of the pyrimidine ring of the compound of Formula I with the amine of Formula VIII to form an amino group at the 6 position of the pyrimidine ring in the resulting compound of Formula XIII.

Accordingly, the method of Scheme 7 provides a method of using a compound of Formula I to prepare a compound of Formula XIII. Also, the combined methods of Schemes 2 and 7 provide a method of using a compound of Formula III to prepare a compound of Formula XIII. Formed compounds may or may not be isolated between combined schemes.

The method of Scheme 7 is illustrated in Example 12.

One embodiment of using a compound of Formula XIII to form a compound of Formula XIV is shown in Scheme 8, as follows:

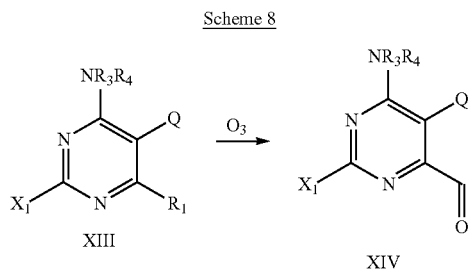

Scheme 8

As shown in Scheme 8, a compound of Formula XIV, i.e., a 6-amino-2-halo-5-alkoxy-pyrimidine-4-carbaldehyde, can be prepared using a compound of Formula XIII, i.e., a 6-amino-2-halo-5-alkoxy-4-substituted pyrimidine. The method of Scheme 8 includes reacting a compound of Formula XIII with an oxidant to form a compound of Formula XIV.

In this case, $X_1$ represents a halogen; Q represents a $C_1$-$C_2$ alkoxy; $R_1$ represents a hydrocarbon chain; and $R_3$ and $R_4$ independently represent H, $C_1$-$C_6$ alkyl, $C_3$-$C_6$ alkenyl, $C_3$-$C_6$ alkynyl, hydroxyl, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, or $C_1$-$C_6$ dialkyl phosphonyl, or $R_3$ and $R_4$ taken together with N represent a 5- or 6-membered saturated ring. The oxidant may be ozone ($O_3$).

The method of Scheme 8 includes contacting the hydrocarbon chain at the 4 position of the pyrimidine ring of the compound of Formula XIII with an oxidant to form a carbonyl group at the 4 position of the pyrimidine ring in the resulting compound of Formula XIV. Thus, the compound of Formula XIV may be the carbaldehyde derivative of the compound of Formula XIII.

The method of Scheme 8 may include introducing the oxidant with one or more solvent(s). The solvent may be a halogenated solvent, e.g., dichloromethane (DCM). The solvent may be methanol.

Accordingly, the method of Scheme 8 provides a method of using a compound of Formula XIII to prepare a compound of Formula XIV. Also, the combined methods of Schemes 7 and 8 provide a method of using a compound of Formula I to prepare a compound of Formula XIV. Also, the combined methods of Schemes 2, 7, and 8 provide a method of using a compound of Formula III to prepare a compound of Formula XIV. Formed compounds may or may not be isolated between combined schemes.

Another embodiment of forming a compound of Formula IX is shown in Scheme 9, as follows:

Scheme 9

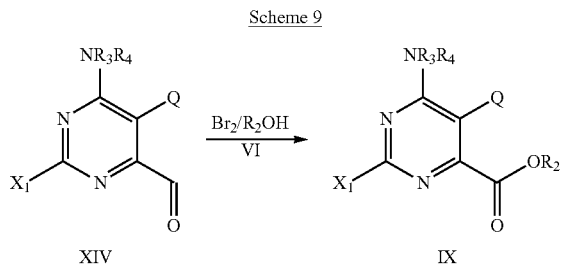

As shown in Scheme 9, a compound of Formula IX, i.e., an alkyl 6-amino-2-halo-5-alkoxy-pyrimidine-4-carboxylate, can be prepared using a compound of Formula XIV, i.e., a 6-amino-2-halo-5-alkoxy-pyrimidine-4-carbaldehyde.

In this case, $X_1$ represents a halogen; Q represents a $C_1$-$C_2$ alkoxy; $R_2$ represents an alkyl; and $R_3$ and $R_4$ independently represent H, $C_1$-$C_6$ alkyl, $C_3$-$C_6$ alkenyl, $C_3$-$C_6$ alkynyl, hydroxyl, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, or $C_1$-$C_6$ dialkyl phosphonyl, or $R_3$ and $R_4$ taken together with N represent a 5- or 6-membered saturated ring.

The method of Scheme 9 includes contacting the carbonyl group at the 4 position of the pyrimidine ring of the compound of Formula XIV with bromine in an alcohol of Formula VI to form a carboalkoxy group at the 4 position of the pyrimidine ring in the resulting compound of Formula IX.

Accordingly, like the method of Scheme 4, the method of Scheme 9 provides a method of preparing a compound of Formula IX. Also, the method of Scheme 9 provides a method of using a compound of Formula XIV to prepare a compound of Formula IX. Also, the combined methods of Schemes 8 and 9 provide a method of using a compound of Formula XIII to prepare a compound of Formula IX. Also, the combined methods of Schemes 7 through 9 provide a method of using a compound of Formula I to prepare a compound of Formula IX. Also, the combined methods of Schemes 2 and 7 through 9 provide a method of using a compound of Formula III to prepare a compound of Formula IX. Formed compounds may or may not be isolated between combined schemes.

It is recognized that some reagents and reaction conditions disclosed herein or in the chemical literature for preparing compounds of Formulas IX, XI, XII, or derivatives thereof, may not be compatible with certain functionalities present in the intermediates. In these instances, the incorporation of protection/deprotection sequences or functional group interconversions into the synthesis will aid in obtaining the desired products. The use and choice of the protection groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of the pyrimidine compounds described above. One skilled in the art will also recognize that it may necessary to perform a combination of the steps disclosed herein or in the chemical literature in an order other than that implied by the particular sequence presented to prepare the pyrimidine compounds described above.

Finally, one skilled in the art will also recognize that pyrimidine compounds described above and the intermediates thereof described herein or in the chemical literature can be subjected to various electrophilic, nucleophilic, radical, organometallic, oxidation, and reduction reactions to add substituents or modify existing substituents.

The compounds of Formula XI have been found to be useful as pre-emergence and post-emergence herbicides. Therefore, the described pyrimidine compounds of Formulas I, II, III, V, VII, IX, XIII, or XIV, or the agriculturally acceptable derivatives thereof, including, for example, pyrimidine compounds of Formula XII, are useful intermediates in the formation of herbicides prepared with compounds of Formula XI or the like. The term herbicide is used herein to mean an active ingredient that kills, controls, or otherwise adversely modifies the growth of plants.

The following examples are presented to illustrate various embodiments of the present disclosure in more detail. These examples are not to be construed as being exhaustive or exclusive as to the scope of this invention.

EXAMPLES

Example 1

Preparation of 2,6-dichloro-5-methoxy-4-vinyl pyrimidine

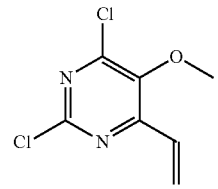

2,6-Dichloro-5-methoxy-6-vinyl pyrimidine may be prepared using 2,6-dichloro-5-methoxy pyrimidine, which is commercially available. To a solution of 2,6-dicholoro-5-methoxy pyrimidine (100 g, 0.55 mol) in dry tetrahydrofuran (THF) solvent was added, dropwise, 1M vinyl magnesium bromide in THF solvent (124 g, 0.94 mol) for one hour at room temperature. The mixture was then stirred for 4 h at room temperature. Excess Grignard reagent was quenched by addition of acetone (200 mL) while the temperature of the mixture was maintained at a temperature below 20° C. Thereafter, 2,3-dichloro-5,6-dicyano-p-benzoquinone (DDQ) (151 g, 0.67 mol) was added at once and stirred overnight. A yellow solid precipitated out. The solid was filtered and washed with ethyl acetate (500 mL) The filtrate was concentrated under reduced pressure and the resulting crude compound was diluted with ethyl acetate (2 L). The resulting undissolved, dark, semi-solid was separated by filtration using ethyl acetate. It was further concentrated under reduced pressure to provide a crude compound, which was purified by column chromatography. The compound was eluted with 5% to 10% ethyl acetate in hexane mixture to provide the title compound (70 g, 60% yield): mp 60-61° C.; $^1$H NMR (CDCl$_3$) δ 3.99 (s, 3H), 5.85 (d, 1H), 6.75 (d, 1H), 6.95 (dd, 1H).

Example 2

Preparation of 2,6-dichloro-5-methoxy-4-vinyl pyrimidine

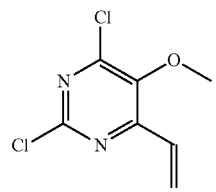

2,6-Dichloro-5-methoxy-6-vinyl pyrimidine may be prepared using 2,6-dichloro-5-methoxy pyrimidine, which is commercially available. 2,6-Dichloro-5-methoxy pyrimidine (12.5 g, 69.8 mmol) was combined in a flask with THF (125 mL) and placed in a room temperature water bath. Vinyl magnesium bromide (78 mL, 76.8 mmol) was added in three portions. The mixture was stirred for 5 h. Acetone was added to quench any remaining Grignard reagent. DDQ (19 g, 83.8 mmol) was added to the mixture, and the mixture was stirred overnight. The mixture was then concentrated to remove the THF. Dichloromethane (DCM) was added, triturated, and allowed to stand over the weekend before being filtered, concentrated, and purified by column chromatography on silica gel using a 5-30% ethyl acetate/hexane gradient. This produced the title compound (7.95 g), which was observed to be a light yellow solid that turned grey in light.

Example 3

Preparation of 2,6-dichloro-5-methoxy-4-vinyl pyrimidine

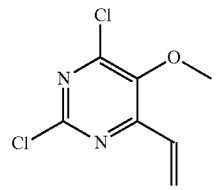

2,6-Dichloro-5-methoxy-6-vinyl pyrimidine may be prepared using 2,6-dichloro-5-methoxy pyrimidine, which is commercially available. 2,6-Dichloro-5-methoxy pyrimidine (10 g, 56 mmol) was dissolved in THF (15 mL). The solution was added dropwise to vinyl magnesium bromide (60 mL of 1 M, 60 mmol) over approximately 15 minutes while keeping the temperature of the mixture below 30° C. by external cooling. Rapid, clean formation of a dihydro-vinyl pyrimidine intermediate (having a molar weight of 206 g/mol) was observed using GC-MS and HPLC. The mixture was stirred for approximately 3 h at room temperature. Conversion of greater than 95% was observed by GC/FID. The mixture was cooled to below 10° C. and treated in portions with citric acid (150 mL of 10% citric acid). It was then diluted with ethyl acetate (75 mL). The phases were separate and the organic phase extracted using ethyl acetate (1×50 mL). The organic phases were then combined and washed with saturated sodium chloride (1×50 mL), then dried, and evaporated to provide a crude dihydro intermediate. This material was dissolved in DCM (200 mL) and treated with manganese dioxide (10.4 g, 120 mmol) while stirred at room temperature. The rapid formation of 2,6-dichloro-5-methoy-4-vinyl pyrimidine (having a molar weight of 204 g/mol) was observed. After about 1 h, an additional amount of manganese dioxide (15 g) was added and the mixture stirred overnight. The manganese dioxide was removed by filtration through celite. The filtrate was washed with DCM and acetone. The filtrate was then concentrated by allowing the solvents to evaporate and purified by column chromatography using silica with a ramp of 0-10% ethyl acetate/hexane. This provided the title compound (approximately 500 mg, approximately 4% yield): mp 59-60° C.

Example 4

Preparation of 2,6-dichloro-5-methoxy-4-allyl pyrimidine

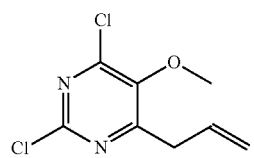

2,6-Dichloro-5-methoxy-6-allyl pyrimidine may be prepared using 2,6-dichloro-5-methoxy pyrimidine, which is commercially available. 2,6-Dichloro-5-methoxy pyrimidine (3.0 g, 17 mmol) was dissolved in THF (30 mL) and treated in portions with allyl magnesium bromide (17 mL of 1M allyl magnesium bromide in diethyl ether, 17 mmol). The resulting reaction was exothermic. External cooling was used to keep the temperature of the mixture below 30° C. After 20 minutes, the mixture was subjected to HPLC and GC-MS. After 45 minutes, the mixture was cooled in ice/salt and the reaction quenched with saturated ammonium chloride (30 mL) then diluted with ethyl acetate (75 mL). The organic phase was washed with saturated sodium chloride (30 mL), dried, and evaporated. The residue was dissolved in 1,4-dioxane (50 mL), treated with DDQ (3.9 g, 17 mmol), and stirred for 20 h. GC-MS showed presence of 2,6-dichloro-5-methoxy-6-allyl pyrimidine (having molar weight of 218 g/mol). The residue was washed in water and ethyl acetate and purified by column chromatography using silica with ethyl acetate and hexane. This provided the title compound (2.5 g, 67% yield): mp 61-62° C. $^1$H NMR (400 MHz, CDCl$_3$) δ 6.07-5.94 (m, 1H), 5.26-5.16 (m, 2H), 3.94-3.89 (s, 3H), 3.65-3.56 (m, 2H)); EIMS m/z 218.

Example 5

Preparation of 2,6-dichloro-5-methoxy-4-furan-2-yl pyrimidine

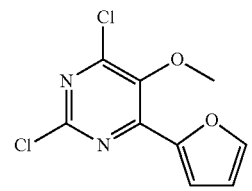

2,6-Dichloro-5-methoxy-4-furan-2-yl pyrimidine may be prepared using 2,6-dichloro-5-methoxy pyrimidine, which is commercially available. Furan (20.4 g, 300 mmol) was dissolved in THF (44 mL) and diethyl ether (88 mL). The furan solution was cooled to about −20° C. and treated in portions with butyllithium (28 mL of 2.5 M, 70 mmol). The furan and butyllithium solution was stirred at −15° to −5° C. for approximately 75 minutes. Magnesium bromide (19 g, 74 mmol) in diethyl ether was added at about −2° C. and stirred for 40 minutes, then cooled to −20° C. This was then added to 2,6-dichloro-5-methoxy pyrimidine (10.0 g, 56 mmol) and stirred at −15° C. to −20° C. for 30 minutes, then warmed to room temperature and stirred for 3 h. The reaction was quenched by the addition of saturated ammonium chloride. DDQ was added, and then the solution was stirred with 15 h. GC-MS showed near complete conversion of the 2,6-dichloro-5-methoxy pyrimidine (with a molar weight of 178 g/mol) to 2,6-dichloro-5-methoxy-4-furan-2-ylpyrimidine (with a molar weight of 244 g/mol). The mixture was diluted by THF (150 mL) and water (100 mL). The pH of the mixture was lowered to acidic levels by the addition of hydrochloric acid (6 M). The organic phase was separated and extracted with an additional 100 mL of ethyl acetate. The combined organic phases were washed with saturated sodium chloride, dried, and concentrated onto silica gel (50 g). The dried material was added to the top of a silica gel column and eluted with a 0% to 30% ethyl acetate/hexane until no further product eluted. This provided the isolated title compound (7.4 g, 55% yield): mp 105-107° C.; $^1$H NMR (400 MHz, CDCl$_3$) δ 7.78-7.66 (d, J=1.7 Hz, 1H), 7.55-7.46 (d, J=3.6 Hz, 1H), 6.71-6.57 (m, 1H), 4.31-3.48 (s, 3H). EIMS m/z 244.

Example 6

Preparation of 2,6-dichloro-5-methoxy-pyrimidine-4-carbaldehyde

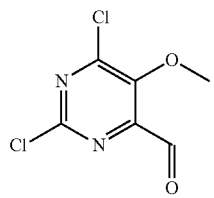

The solution of 2,6-dichloro-5-methoxy-4-vinyl pyrimidine (50 g, 0.24 mol) in dichloromethane:methanol (4:1, 2 L), prepared by Example 1, was cooled to −78° C. Ozone gas was bubbled through for 5 h. The reaction was quenched with dimethyl sulfide (50 mL). The mixture was slowly warmed to room temperature and concentrated under reduced pressure at 40° C. to provide a crude material comprising the title compound (50.5 g, 100% yield); HPLC (85% acetonitrile buffered with 0.1% v/v acetic acid. The title compound was not isolated from the crude material.

Example 7

Preparation of 2,6-dichloro-5-methoxy-pyrimidine-4-carbaldehyde

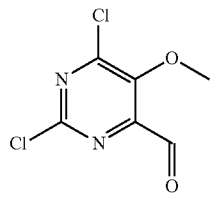

A solution of 2,6-dichloro-5-methoxy-4-vinyl pyrimidine (6.64 g, 32.5 mmol, prepared by Example 2), in methanol:dichloromethane (1:4, 300 mL), was cooled to −78° C. in a dry ice/acetone bath. Ozone was bubbled into the reaction until the starting material was no longer present according to thin layer chromatography (TLC). Dimethyl sulfide (6 mL) was added. The mixture was concentrated on a rotary evaporator at 0° C. to remove the dichloromethane. This provided an unpurified material comprising the title compound. The title compound was not isolated from the unpurified material.

Example 8

Preparation of methyl 2,6-dichloro-5-methoxy-pyrimidine-4-carboxylate

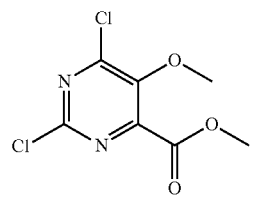

A solution of 2,6-dichloro-5-methoxy-pyrimidine-4-carbaldehyde (see Examples 6 and 7 above for methods for preparing this compound) (50 g, 0.24 mol) in methanol (1 L) and water (60 mL) was prepared. To the solution, sodium bicarbonate (400 g) was added. A 2 M solution of bromine (192 g, 1.2 mol) in methanol/water (600 mL, 9:1) was added, dropwise, to the pyrimidine solution for 45 minutes at 0° C. while stirring the mixture. The stirring was continued at the same temperature for 1 h. Later, the mixture was stirred at room temperature for 4 h. While stirring, the reaction mixture was thereafter poured onto a mixture of crushed ice (2 L), sodium bisulfite (50 g), and sodium chloride (200 g). The product was extracted with ethyl acetate (1 L×2), and the combined organic layer was dried over sodium sulfate and filtered. Evaporation of the solvent under reduced pressure produced a thick material, which was then solidified on long standing. This produced the title compound (50.8 g, 87% yield); LC-MS 238 (m+1); HPLC (95% acetonitrile buffered with 0.1% v/v acetic acid.

Example 9

Preparation of methyl 2,6-dichloro-5-methoxy-pyrimidine-4-carboxylate

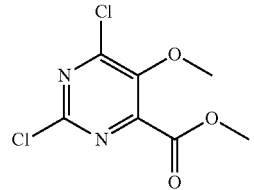

The 2,6-dichloro-5-methoxy-pyrimidine-4-carbaldehyde crude material (32.5 mmol), prepared by Example 7, was cooled to 0° C. in an ice/water bath. It was assumed that approximately 60 mL of methanol was still present in the crude material. Additional methanol (60 mL) and water (13 mL) was added to the chilled crude material. Solid sodium bicarbonate (54.7 g) was added, and the solution stirred vigorously. A 2 M solution of bromine (81.4 mL, 163 mmol) in methanol and water (9:1) was dropwise added to the crude material solution over 30 minutes. The reacting mixture was stirred at 0° C. for 1 h. The mixture was then removed from the ice/water bath, and the reaction monitored using GCMS. About 6 h after initiating the reaction with bromine, a mixture of Na₂S₂O₃.5H₂O (4.5 g), saturated NaCl (150 mL), and ice (400 g) was prepared and, into this, the reaction mixture was poured. This was diluted with ethyl acetate (200 mL), and additional ethyl acetate (200 mL) was used to extract the product. The combined organic phases were dried over sodium sulfate, filtered, and toluene (50 mL) was then added. The product was then concentrated on a rotary evaporator with a bath temperature of less than or equal to 25° C. Obtained was a yellow oil comprising the title compound (3.1 g, 45% yield). The title compound was not isolated from the solution.

Example 10

Preparation of methyl 6-amino-2-chloro-5-methoxy-pyrimidine-4-carboxylate

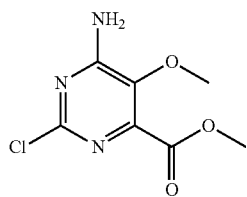

A solution comprising the reaction mixture prepared by Example 8, which reaction mixture contained the methyl 2,6-dichloro-5-methoxy-pyrimidine-4-carboxylate (25 g, 0.1 mol), and dimethyl sulfoxide (DMSO) was prepared. To this solution was added, at 0-5° C., a solution of ammonia in DMSO (2 eq). This mixture was stirred at the same 0-5° C. temperature for 10 to 15 minutes. Later, the mixture was diluted with ethyl acetate, and the resulting solid was filtered. The filtrate was washed with a brine solution. The organic layer was dried over sodium sulfate. Upon concentration, the crude product was obtained. The crude product was stirred in a minimum amount of ethyl acetate and filtered to obtain the pure compound. The resulting filtrate, after concentration, was column purified. This produced the title compound (11 g, 50% yield): mp 158° C.; ¹H NMR (DMSO-d6) δ 3.71 (s, 3H), 3.86 (s, 3H), 7.65 (brs, 1H), 8.01 (brs, 1H).

Example 11

Preparation of methyl 6-amino-2-chloro-5-methoxy-pyrimidine-4-carboxylate

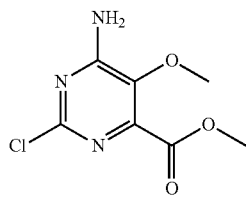

To a solution comprising the reaction mixture (3.1 g) prepared by Example 9, which reaction mixture contained the methyl 2,6-dichloro-5-methoxy-pyrimidine-4-carboxylate (approximately 32.5 mmol), was added DMSO (33 mL). This mixture was cooled to 0° C. in an ice/water bath. Ammonia was bubbled through the mixture in 1 minute intervals. The resulting reaction was followed by TLC, checking for consumption of the starting material. The reaction mixture was diluted with ethyl acetate (200 mL) and then filtered. The organic phase was then washed with saturated sodium chloride and a 50% ethyl acetate, 50% hexane solution. Then it was back extracted with ethyl acetate (200 mL). The organic phases were combined and dried over sodium sulfate, filtered, and concentrated. Then a minimum amount of ethyl acetate was added before further filtering. The resulting filtrate was dripped into hexane (500 mL) and then filtered again. The resulting filtrate was concentrated and saved. This produced the title compound (1.38 g).

Example 12

Preparation of 6-amino-2-chloro-5-methoxy-4-furan-2-yl pyrimidine

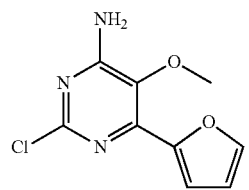

2,6-Dichloro-5-methoxy-4-furan-2-ylpyrimidine (500 mg, 2.0 mmol) (see Example 5 for the preparation of 2,6-dicholor-5-methoxy-4-furan-2-yl pyrimidine) was dissolved in dry DMSO (10 mL) and heated to 60° C. This mixture was treated with a gentle stream of ammonia. After approximately 2 h, conversion was complete to about a 95:5 ratio of mono-amino isomers (having a molar weight of 225 g/mol). This mixture was cooled and diluted with water (50 mL), and the product extracted with ethyl acetate (2×50 mL). Then, the product was washed with ethyl acetate, twice with water (25 mL), and once with saturated sodium chloride (25 mL). The result was dried and concentrated. The product was purified by column chromatography using silica with a 5 to 20% ramp of ethyl acetate/hexane to give the title compound (400 mg, 89% yield). The various isomers were not separated.

Example 13

Preparation of 2-chloro-5-methoxy-6-vinylpyrimidin-4-amine

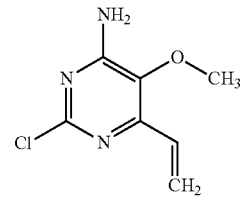

A solution of 2,6-dichloro-5-methoxy-6-vinyl pyrimidine (which is prepared as described in Example 2), and dimethyl sulfoxide (DMSO) is prepared. To this solution is added, at 0-5° C., a solution of ammonia in DMSO (2 eq). This mixture is stirred at the same 0-5° C. temperature for 10 to 15 minutes. Later, the mixture is diluted with ethyl acetate, and the resulting solid is filtered. The filtrate is washed with a brine solution. The organic layer is dried over sodium sulfate. Upon concentration, the crude product is obtained. The crude product is stirred in a minimum amount of ethyl acetate and filtered to obtain the pure compound. The resulting filtrate, after concentration, is column purified. This produces the title compound.

Example 14

Preparation of 6-amino-2-chloro-5-methoxypyrimidine-4-carbaldehyde

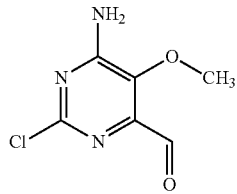

A solution of 2-chloro-5-methoxy-6-vinylpyrimidin-4-in methanol:dichloromethane (1:4), is cooled to −78° C. in a dry ice/acetone bath. Ozone is bubbled into the reaction until the starting material is no longer present according to thin layer chromatography (TLC). Dimethyl sulfide is added. The mixture is concentrated on a rotary evaporator at 0° C. to remove the dichloromethane. This provides a crude material comprising the title compound.

Example 15

Preparation of methyl 6-amino-2-chloro-5-methoxypyrimidine-4-carboxylate

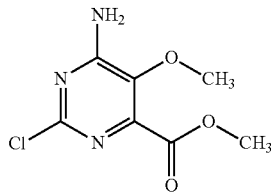

A solution of 6-amino-2-chloro-5-methoxypyrimidine-4-carbaldehyde in methanol (1 L) and water is prepared. To the solution, sodium bicarbonate is added. A 2 M solution of bromine in methanol/water (9:1) is added, dropwise, to the pyrimidine solution for 45 minutes at 0° C. while stirring the mixture. The stirring is continued at the same temperature for 1 h. Later, the mixture is stirred at room temperature for 4 h. While stirring, the reaction mixture is poured onto a mixture of crushed ice, sodium bisulfite, and sodium chloride. The product is extracted with ethyl acetate, and the combined organic layer is dried over sodium sulfate and filtered. Evaporation of the solvent under reduced pressure produces the title compound.

While the invention may be susceptible to various modifications and alternative forms, specific embodiments have been described by way of example in detail herein. However, it should be understood that the invention is not intended to be limited to the particular forms disclosed. Rather, the invention is to cover all modifications, equivalents, and alternatives falling within the scope of the invention as defined by the following appended claims and their legal equivalents.

What is claimed is:

1. A method of forming a 2,6-dihalo-5-alkoxy-pyrimdine-4-carbaldehyde comprising reacting a 2,6-dihalo-5-alkoxy-4-substituted pyrimidine with an oxidant.

2. The method of claim 1 wherein reacting a 2,6-dihalo-5-alkoxy-4-substituted pyrimidine with an oxidant comprises reacting the 2,6-dihalo-5-alkoxy-4-substituted pyrimidine with ozone.

3. The method of claim 1 wherein reacting a 2,6-dihalo-5-alkoxy-4-substituted pyrimidine with an oxidant comprises reacting a 2,6-dichloro-5-methoxy-4-vinylic pyrimidine with ozone to form a 2,6-dichloro-5-methoxy-pyrimidine-4-carbaldehyde.

4. A method of forming a 2,6-dihalo-5-alkoxy-4-substituted pyrimidine comprising:
reacting a 2,6-dihalo-5-alkoxy pyrimidine with an organometallic halide reagent to form a 2,6-dihalo-5-alkoxy-4-substituted-3-(metal-halo or metal) pyrimidine; and
oxidizing the 2,6-dihalo-5-alkoxy-4-substituted-3-(metal-halo or metal) pyrimidine to form the 2,6-dihalo-5-alkoxy-4-substituted pyrimidine.

5. The method of claim 4, wherein reacting a 2,6-dihalo-5-alkoxy pyrimidine with an organometallic halide reagent comprises reacting a 2,6-dihalo-5-alkoxy pyrimidine with a Grignard reagent.

6. The method of claim 5, wherein reacting a 2,6-dihalo-5-alkoxy pyrimidine with a Grignard reagent comprises reacting a 2,6-dihalo-5-alkoxy pyrimidine with a vinyl magnesium bromide.

7. The method of claim 4, wherein reacting a 2,6-dihalo-5-alkoxy pyrimidine with an organometallic halide reagent comprises reacting a 2,6-dihalo-5-alkoxy pyrimidine with an organolithium reagent.

8. The method of claim 4, wherein oxidizing the 2,6-dihalo-5-alkoxy-4-substituted-3-(metal-halo or metal) pyrimidine comprises reacting the 2,6-dihalo-5-alkoxy-4-substituted-3-(metal-halo or metal) pyrimidine with 2,3-dichloro-5,6-dicyano-p-benzoquinone.

9. A method of using a 2,6-dihalo-5-alkoxy-4-substituted pyrimidine to form an herbicide, the 2,6-dihalo-5-alkoxy-4-substituted pyrimidine comprising a pyrimidine ring having a 4 position and a 6 position, the pyrimidine ring further comprising a hydrocarbon chain at the 4 position and a halogen at the 6 position, the method comprising:
contacting the hydrocarbon chain at the 4 position with an oxidant to form a carbonyl group at the 4 position;
contacting the carbonyl group at the 4 position with bromine in an alcohol to form a carboalkoxy group at the 4 position; and
contacting the halogen at the 6 position with an amine to form an amino group at the 6 position.

10. The method of claim 9, wherein contacting the hydrocarbon chain at the 4 position with an oxidant comprises contacting the hydrocarbon chain at the 4 position of the pyrimidine ring of the 2,6-dihalo-5-alkoxy-4-substituted pyrimidine with ozone to form 2,6-dihalo-5-alkoxy-pyrimidine-4-carbaldehyde comprising the pyrimidine ring comprising the carbonyl group at the 4 position.

11. The method of claim 10, wherein contacting the carbonyl group at the 4 position with bromine in an alcohol comprises contacting the carbonyl group at the 4 position of the pyrimidine ring of the 2,6-dihalo-5-alkoxy-pyrimidine-4-carbaldehyde with bromine in the alcohol to form alkyl 2,6-dihalo-5-alkoxy-pyrimidine-4-carboxylate comprising the pyrimidine ring comprising the carboalkoxy group at the 4 position and the halogen at the 6 position.

12. The method of claim 11, wherein contacting the halogen at the 6 position with an amine comprises contacting the halogen at the 6 position of the pyrimidine ring of the alkyl 2,6-dihalo-5-alkoxy-pyrimidine-4-carboxylate with amine to form an alkyl 6-amino-2-halo-5-alkoxy-pyrimidine-4-carboxylate comprising the pyrimidine ring comprising the amino group at the 6 position.

13. The method of claim 9, wherein contacting the halogen at the 6 position with an amine comprises contacting the halogen at the 6 position of the pyrimidine ring of the 2,6-dihalo-5-alkoxy-4-substituted pyrimidine with the amine to form a 6-amino-2-halo-5-alkoxy-4-substituted pyrimidine comprising the pyrimidine ring comprising the amino group at the 6 position and the hydrocarbon chain at the 4 position.

14. The method of claim 13, wherein contacting the hydrocarbon chain at the 4 position with an oxidant comprises contacting the hydrocarbon chain of the 6-amino-2-halo-5-alkoxy-4-substituted pyrimidine with an oxidant to form a 6-amino-2-halo-5-alkoxy-pyrimidine-4-carbaldehyde comprising the pyrimidine ring comprising the carbonyl group at the 4 position.

15. The method of claim 14, wherein contacting the carbonyl group at the 4 position with bromine in an alcohol comprises contacting the carbonyl group at the 4 position of the 6-amino-2-halo-5-alkoxy-pyrimidine-4-carbaldehyde with bromine in an alcohol to form alkyl 6-amino-2-halo-5-alkoxy-pyrimidine-4-carboxylate comprising the pyrimidine ring comprising the carboalkoxy group at the 4 position.

16. A method of using 2,6-dihalo-5-alkoxy-4-substituted pyrimidine to form a 2,6-dihalo-5-alkoxy-pyrimidine-4-carboxylic acid, the 2,6 dihalo-5-alkoxy-4-substituted pyrimidine comprising a pyrimidine ring comprising a 4 position, the pyrimidine ring comprising a hydrocarbon chain at the 4 position, the method comprising contacting the hydrocarbon chain at the 4 position with an oxidant to form a carboxyl group at the 4 position.

* * * * *